United States Patent [19]
Kragten et al.

[11] Patent Number: 5,905,173
[45] Date of Patent: May 18, 1999

[54] PROCESS FOR DECOMPOSING CYCLOALKYL HYDROPEROXIDE

[75] Inventors: Ubaldus F. Kragten, Beek; Henricus A.C. Baur, Roermond; Johannes G.H.M. Housmans, Maasbracht, all of Netherlands

[73] Assignee: DSM NV, Heerlen, Netherlands

[21] Appl. No.: 08/729,511

[22] Filed: Oct. 11, 1996

[30] Foreign Application Priority Data

Oct. 13, 1995 [BE] Belgium ................................ 9500853

[51] Int. Cl.$^6$ ............................................. C07C 45/53
[52] U.S. Cl. ........................ 568/342; 568/832; 568/835
[58] Field of Search .................................. 568/342, 385, 568/832, 835

[56] References Cited

U.S. PATENT DOCUMENTS

| | | | |
|---|---|---|---|
| 4,238,415 | 12/1980 | Bryan | 568/342 |
| 4,408,083 | 10/1984 | Toyoura et al. | 568/576 |
| 5,206,441 | 4/1993 | Reimer | 568/342 |

FOREIGN PATENT DOCUMENTS

| | | | |
|---|---|---|---|
| 0 004 105 | 9/1979 | European Pat. Off. | 568/342 |
| 0 092 867 | 11/1983 | European Pat. Off. | 568/342 |
| 0 659 726 | 6/1995 | European Pat. Off. | 568/342 |
| 2 140 088 | 1/1973 | France | 568/342 |

*Primary Examiner*—James H. Reamer
*Attorney, Agent, or Firm*—Pillsbury Madison & Sutro LLP

[57] ABSTRACT

The invention relates to a process for decomposing a mixture containing cycloalkyl hydroperoxide with an aqueous phase containing alkali metal hydroxide where, besides the alkali metal hydroxide, there is also at least 10 wt. % of the aqueous phase of one or more alkali metal salts. The alkali metal salts are preferably alkali metal carbonates, or alkali metal salts of mono- and poly-carboxylic acids, with the carboxylic acid moiety containing 1–24 carbon atoms.

12 Claims, No Drawings

PROCESS FOR DECOMPOSING CYCLOALKYL HYDROPEROXIDE

BACKGROUND OF THE INVENTION

1. Field of the Invention

The invention relates to a process for decomposing a mixture containing cycloalkyl hydroperoxide with an aqueous phase containing alkali metal hydroxide where, besides the alkali metal hydroxide, there is also at least 10% by weight of the aqueous phase of one or more alkali metal salts.

2. Description of the Related Art

A process for decomposing cycloalkyl hydroperoxide has been described in U.S. Pat. No. 4,238,415, which disclosed the decomposition of cycloalkyl peroxide in the presence of sodium hydroxide. The disclosure of this patent, as well as any other printed publication cited by the present specification, is incorporated by reference herein. Although high conversions to cycloalkanones and cycloalkanols were achieved, the reaction velocity is relatively low.

The reaction velocity constant, a measure of the reaction velocity, is an important parameter to increase. The larger this constant, the more efficient is the decomposition reaction. In many cases, this also implies that the contributions of side reactions yielding undesired products is less. In addition, the decomposition reaction can be carried out in a smaller reactor, which means a lower investment, or in an existing reactor in which more of the desired decomposition products, i.e. cycloalkanones and cycloalkanols, can be formed. The cycloalkanones and cycloalkanols can be used in the preparation of caprolactam, which in turn can be used as a raw material in the production of nylons.

SUMMARY OF THE INVENTION

An objective of the invention is to provide a process having a greater reaction velocity for decomposing cycloalkyl hydroperoxide into the desired products cycloalkanol and cycloalkanone. This is achieved by decomposing cycloalkyl hydroperoxide with an aqueous phase containing alkali metal hydroxide and at least one alkali metal salt. The alkali metal salts are preferably soluble and used at a concentration of at least 10% by weight (wt. %) of the aqueous phase.

The invention can decompose cycloalkyl hydroperoxide by mixing an organic phase containing the cycloalkyl hydroperoxide with an aqueous phase containing alkali metal hydroxide and at least one alkali metal salt, wherein the alkali metal salt is at least 10% by weight of the aqueous phase. Enough alkali metal hydroxide may be used so the final [OH$^-$] may be preferably between about 0.1 N and about 2 N. The alkali metal salt may be an alkali metal carbonate or an alkali metal salt of a mono- or polycarboxylic acid, with the carboxylic acid moiety containing 1–24 carbon atoms. The alkali metal salt may also be a sodium or a potassium salt. The salt concentration is preferably less than 45% by weight of the aqueous phase, more preferably between about 20% and about 35% by weight. The ratio between the volume of aqueous phase and the volume of organic phase may be greater than about 0.02.

After decomposition of cycloalkyl hydroperoxide is completed, the reaction mixture can be separated and the aqueous phase can be reused to decompose more cycloalkyl hydroperoxide.

Decomposition of cycloalkyl hydroperoxide can be catalyzed by optionally adding a salt of a transition metal. The transition metal can be cobalt, chromium, manganese, iron, nickel, copper, or combinations of these metals; the amount of transition metal salt used as a catalyst can be between about 0.1 parts per million (ppm) and about 1000 ppm.

The cycloalkyl hydroperoxide for decomposition may be obtained by oxidizing a corresponding cycloalkane at a temperature between about 120° C. and about 200° C. and a pressure between about 3 bar and about 50 bar, wherein no oxidation catalyst is present. Alternatively, the cycloalkyl hydroperoxide may be obtained by catalytic oxidation of the corresponding cycloalkane. The products of the decomposition, cyclalkanone and cycloalkanol, may be recovered for use in other synthetic processes.

The advantages of the invention include an increase in the reaction velocity of the decomposition reaction, which is reflected in greater process efficiency and increased specificity in decomposition products. Smaller reactors can be used or greater yields of product can be achieved.

DETAILED DESCRIPTION OF THE INVENTION

The invention relates to a process for decomposing cycloalkyl hydroperoxide with 5–12 ring carbon atoms using alkali metal hydroxide and at least one alkali metal salt dissolved in an aqueous phase, the amount of alkali metal salt used being at least 10 wt. % of the aqueous phase.

The alkali metal salts used for this purpose are preferably soluble alkali metal salts. Suitable salts are alkali metal acetates, alkali metal carbonates and, in particular, alkali metal carboxylates. Alkali metal salts of mono- and polycarboxylic acids in which the carboxylic acid moiety preferably comprises 1–24 carbon atoms are suitable; more preferably, the carboxylic acid moiety comprises 1–12 carbon atoms. Poly-carboxylates include, for instance, the di-carboxylates, tri-carboxylates, and tetra-carboxylates. Suitable alkali metals are sodium and potassium. Preferably, the alkali metal is sodium. Examples of suitable carboxylic acids useful in making alkali metal salts include acetic acid, propionic acid, butyric acid, adipic acid, hexanoic acid, pentanoic acid, propane dicarboxylic acid, hexane dicarboxylic acid, stearic acid, decanoic acid, and decane dicarboxylic acid. Special preference is given to the use of mixtures of different carboxylic acids, since these are simple to obtain.

The quantity of alkali metal salts used is at least about 10 wt. % alkali metal salt based on the aqueous phase that is present, which is separate from the organic phase containing the cycloalkyl hydroperoxide. Total salt concentration is preferably higher than about 15 wt. %; also, the total salt concentration is preferably lower than about 35 wt. %. More preferably, the total salt concentration used is between about 20 and about 35 wt. %. A higher total salt concentration, for instance about 45 wt. %, can also be used. However, this has the disadvantage that crystallization of metal carboxylates may occur when the process stream is cooled. This can be prevented by diluting the process stream.

The mixture containing cycloalkyl hydroperoxide can be obtained by liquid phase oxidation of the corresponding cycloalkane with an oxygen-containing gas. Cycloalkanes are preferably cyclopentane, cyclooctane, cyclododecane and, more preferably, cyclohexane. The oxidation mixture formed may contain other peroxides besides the cycloalkyl hydroperoxide, for example dicycloalkyl peroxide. Suitable methods for preparing cyclohexyl hydroperoxide are disclosed in U.S. Pat. Nos. 4,238,415, 4,918,249, 5,043,481, 5,068,464, and 5,126,505, the complete disclosures of which are incorporated herein by reference.

The oxidation takes place in the liquid phase using an oxygen-containing gas such as air or pure oxygen. Suitable oxidation temperatures are between about 120° C. and about 200° C. Preferably, a temperature between about 140° C. and about 190° C. is used. The reaction is carried out for 5 minutes to 24 hours. The pressure must be such that a liquid phase is maintained in the system. The pressure is usually between about 3 bar and about 50 bar, preferably between about 4 bar and about 25 bar.

Preferably, the oxidation is operated continuously and takes place in a system of series-arranged reactors or a tubular reactor (see pp. 4–24 to 4–27 of Perry's Chemical Engineers' Handbook, Sixth Edition, McGraw-Hill, New York, 1984 for descriptions of chemical reactors). Other suitable reactors are disclosed in "Chemical Reaction Engineering" (chapters 4 and 5) by Octave Levenspiel and "Chemical Reactor Design and Operation" (chapter 8) by Westerterp et al. Usually, the reaction is operated autothermally or via temperature control. Temperature control usually takes place by discharging the reaction heat via a gas stream, intermediate cooling, or using other methods known to one skilled in the art. To prevent transition metals (which promote the decomposition of cycloalkyl hydroperoxide) from entering the mixture to be oxidized, reactors with inert internal walls may be used. For instance, use can be made of reactors with internal walls made of passivated steel, aluminium, tantalum, glass or enamel. This is especially important for small production capacities where, for example, the ratio between wall area and liquid volume is unfavorable. For large capacities, a reactor with inert internal walls is not required. It should be clear that, if a negligible quantity of metal ions enters the oxidation mixture, this does not have any substantial effect on the reaction, and in the context of this invention noncatalyzed cycloalkane oxidation may be used.

In contrast to noncatalyzed cycloalkane oxidation, catalyzed oxidation by a metal such as cobalt and chromium, as disclosed in U.S. Pat. Nos. 3,987,101 and 4,042,630, the complete disclosures of which are incorporated herein by reference, results in a high rate of conversion that produces a reaction mixture with a relatively small quantity of cycloalkyl hydroperoxide remaining compared with the quantity of cycloalkanone and cycloalkanol produced. Notwithstanding this, the process according to the invention is also advantageous in catalyzed oxidation where only a small quantity of cycloalkyl hydroperoxide remains.

Usually the product of the noncatalyzed oxidation of cyclohexane contains at least comparable quantities, in weight percentage (wt. %), of cyclohexyl hydroperoxide and of cyclohexanol plus cyclohexanone. Often, the mixture after the oxidation reaction contains a quantity of cyclohexyl hydroperoxide that is more than twice the quantity of cyclohexanol plus cyclohexanone. In contrast, catalyzed oxidation produces a mixture which contains less than 50 wt. % cyclohexyl hydroperoxide compared with the weight percentage of cyclohexanol plus cyclohexanone. Often, there is even less than 40 wt. % cyclohexyl hydroperoxide compared with the weight percentage of cyclohexanol plus cyclohexanone.

The cycloalkyl hydroperoxide concentration in the reaction mixture as it leaves the last oxidation reactor is generally between about 0.1 wt. % and about 8.0 wt. %. The cycloalkanol concentration in this mixture is generally between about 0.1 wt. % and about 10 wt. %. The cycloalkane conversion relative to this reaction mixture is generally between about 0.5 wt. % and about 25 wt. %. For example, cyclohexane conversion is generally between about 2 wt. % and about 6 wt. %.

For the decomposition of cycloalkyl hydroperoxide, enough alkali metal hydroxide is added so that the [OH⁻] of the aqueous phase on completion of decomposition is at least 0.1 N, preferably at least 0.6 N. Completion of decomposition means greater than 90% conversion. In principle, an [OH⁻] higher than 2 N is possible, but this does not offer any advantages. Such a high concentration might result in side-reactions occurring, for instance aldol condensations of cyclohexanone. Therefore, the quantity of alkali metal hydroxide used is preferably such that the [OH⁻] upon completion is between about 0.1 N and about 2 N. More preferably, enough hydroxide is used such that the [OH⁻] at completion is between about 0.6 N and about 1 N. Preferred alkali metal hydroxides for the process according to this invention are sodium hydroxide and potassium hydroxide.

The decomposition reaction of cycloalkyl hydroperoxide is preferably carried out in the presence of at least one catalyst, a cycloalkyl hydroperoxide decomposition-promoting metal salt. This is generally a salt of a transition metal (e.g., Groups IB, VIB, VIIB and VIIIB of the Periodic Table). Examples of suitable transition metals are cobalt, chromium, manganese, iron, nickel, copper, or mixtures of these metals, such as for instance a mixture of cobalt and chromium. Preferably, the transition metal salt is water soluble. The metal sulphates, metal acetates, and metal carboxylates (e.g., benzoate) are suitable salts. Besides sulphates, nitrates and chlorides can be used, although they have the disadvantage of often being corrosive. Complex salts such as, for example, potassium chromate can, in principle, be used. The quantity of transition metal salt can be about 0.1 ppm to about 1000 ppm, calculated as transition metal relative to the weight of the aqueous phase. However, it is also possible to use larger quantities of transition metal salt. Preferably, the transition metal salt is present between about 0.1 ppm and about 10 ppm.

The transition metal salt can be added, optionally in combination with the alkali metal hydroxide, as an aqueous solution to the mixture containing the cycloalkyl hydroperoxide. It is also possible to add the transition metal as an organic salt, dissolved in an organic solvent, to the reaction mixture in an amount such that the concentration of transition metal salt in the aqueous phase after phase separation is within the ranges given above. For example, the cycloalkane corresponding to the cycloalkyl hydroperoxide may be used as an organic solvent. Benzene and cyclohexene are other suitable organic solvents.

Other peroxides (e.g., dicycloalkyl peroxides) that may be present in the mixture are also decomposed.

The decomposition reaction takes place by allowing the cycloalkyl hydroperoxide-containing mixture to react for about 5 minutes to about 300 minutes. Preferably, the residence time in the decomposition reactor is about 15 minutes to about 120 minutes, but the time needed can be simply determined by one skilled in the art according to the desired amount of conversion.

The decomposition reaction preferably takes place in a plug reactor or tubular reactor, provided that sufficient mixing of the liquid phases is established by, for example, means of stirring gear or a static mixer (see pp. 4–24 to 4–25 of "Perry's Chemical Engineers' Handbook").

To achieve efficient cycloalkyl hydroperoxide decomposition, the volume ratio between the aqueous phase and the organic phase in the decomposition reactor is preferably greater than 0.02. Preferably, a ratio of about 0.05 to about 0.25 is used. However, these volume ratios are not critical and can, if desired, be adjusted by one skilled in the art.

The cycloalkyl hydroperoxide decomposition can take place at a temperature between about 60° C. and about 180° C. Preferably, the decomposition takes place at a temperature between about 60° C. and about 100° C.

The decomposition reaction can be carried out either at atmospheric or at an elevated pressure, such as about 1 bar to 6 bar. The decomposition of cycloalkyl hydroperoxide can advantageously be carried out at a pressure that is of the same order as the pressure used for oxidation of the corresponding cycloalkane; however, it may also be advantageous to evaporate part of the cycloalkane after oxidation by reducing the pressure (i.e., flashing). The pressure during the decomposition reaction is then preferably about 1 bar to about 6 bar, more preferably the decomposition reaction is carried out at atmospheric pressure. The two reactions can be controlled to ensure that decomposition does not occur before oxidation is completed.

After decomposition, the aqueous phase can be separated from the organic phase. The organic phase can then be washed to remove trace residues of salt contained in the aqueous phase. The aqueous phase can be reused in the decomposition reaction if it satisfies the above-mentioned requirements. The aqueous phase already contains alkali metal salts of mono- or poly-carboxylic acids but, often, addition of alkali metal hydroxide is necessary. The carboxylic acids can be formed as a by-product of the oxidation or the decomposition reaction, where in the presence of alkali metal, a salt is formed with the carboxylic acid. Reuse of the aqueous phase has the advantage that the ratio between aqueous phase and organic phase can be set and monitored in a simple manner.

Distillation of the organic phase eventually yields a mixture of cycloalkanone and cycloalkanol.

The decomposition reaction can be carried out either continuously or batchwise.

This process for decomposing cycloalkyl hydroperoxides has been disclosed in Belgian Patent Application No. 9500853, filed Oct. 13, 1995, the entire contents of which are hereby incorporated by reference and relied upon. Moreover, all journal articles, texts, and patents cited in this specification are incorporated by reference in their entirety.

The following examples are meant to be illustrative of the present invention, however the practice of the invention is not limited or restricted in any way by the exemplified reactions.

EXAMPLES

Example I

At a temperature of 70° C., 107 ml of an aqueous phase containing dissolved NaOH (1500 mmol NaOH/kg) and sodium acetate (15 wt. %) was added to 250 ml of a cyclohexane oxidation mixture containing, per kilogram, 190 mmol cyclohexyl hydroperoxide (CHHP), 40 mmol cyclohexanone (ON) and 90 mmol cyclohexanol (OL). Decomposition of the CHHP was monitored by means of an iodometric titration. The first-order velocity constant was $11*10^{-3}$ min$^{-1}$.

Comparative Example A

Example I was repeated with 107 ml of an aqueous phase containing dissolved NaOH (1500 mmol NaOH/kg) being added. Decomposition of the CHHP was monitored by means of an iodometric titration. The first-order velocity constant was $8*10^{-3}$ min$^{-1}$.

Example II

At a temperature of 70° C., 107 ml of an aqueous phase containing dissolved NaOH (1500 mmol NaOH/kg), sodium acetate (15 wt. %) and Cr(NO$_3$)$_3$ (10 ppm Cr) was added to 250 ml of a cyclohexane oxidation mixture containing, per kilogram, 190 mmol cyclohexyl hydroperoxide (CHHP), 40 mmol cyclohexanone (ON) and 90 mmol cyclohexanol (OL). Decomposition of the CHHP was monitored by means of an iodometric titration. The first-order velocity constant was $13*10^{-3}$ min$^{-1}$.

Comparative Example B

Example II was repeated, except that 107 ml of an aqueous phase containing dissolved NaOH (1500 mmol NaOH/kg) and Cr (NO$_3$)$_3$ (10 ppm Cr) was added. Decomposition of the CHHP was monitored by means of an iodometric titration. The first-order velocity constant was $8*10^{-3}$ min$^{-1}$.

Continuous Reactions In a Glass Reactor

Procedure

The reaction took place in two double-walled glass reactors arranged in series, with a liquid volume per reactor of 500 ml. Both reactors were provided with baffles, stirrer, reflux cooler and an overflow. Fresh oxidate and fresh aqueous phase were introduced through the first reactor. The temperature in both reactors was controlled by two independent thermostats.

Example III

The first reactor was fed at 17.0 ml/min with a cyclohexane oxidation mixture containing, per kilogram, 153 mmol cyclohexyl hydroperoxide (CHHP), 53 mmol cyclohexanone (ON) and 105 mmol cyclohexanol (OL). In addition, 1.95 ml/min of an aqueous phase was added which contained dissolved NaOH (750 mmol NaOH/kg), Na$_2$CO$_3$ (354 mmol Na$_2$CO$_3$/kg), CoSO$_4$ (4.3 ppm Co) and a mixture of sodium salts of mono- and di-carboxylic acids (C$_1$ through C$_6$) (20 wt. % in water). Decomposition of the CHHP took place at a temperature of 69° C. in the first reactor and a temperature of 66° C. in the second reactor. Decomposition of the CHHP was monitored by means of an iodometric titration. The first-order velocity constant, calculated over both reactors, was $140*10^{-3}$ min$^{-1}$. CHHP conversion exceeded 95%.

Example IV

Example III was repeated, except that the first reactor was fed at 16.7 ml/min with a cyclohexane oxidation mixture containing, per kilogram, 182 mmol cyclohexyl hydroperoxide (CHHP), 42 mmol cyclohexanone (ON) and 86 mmol cyclohexanol (OL). In addition, 1.93 ml/min of an aqueous phase was added which contained dissolved NaOH (750 mmol NaOH/kg), Na$_2$CO$_3$ (365 mmol Na$_2$CO$_3$/kg), CoSO$_4$ (4.3 ppm Co) and a mixture of sodium salts of mono- and di-carboxylic acids (C$_1$ through C$_6$) (20 wt. % in water). Decomposition of the CHHP took place at a temperature of 67° C. in the first reactor and a temperature of 66° C. in the second reactor. Decomposition of the CHHP was monitored by means of an iodometric titration. The first-order velocity constant, calculated over both reactors, was $131*10^{-3}$ min$^{-1}$. CHHP conversion exceeded 95%.

Example V

Example III was repeated, except that the first reactor was fed at 16.9 ml/min with a cyclohexane oxidation mixture containing, per kilogram, 182 mmol cyclohexyl hydroperoxide (CHHP), 42 mmol cyclohexanone (ON) and 86 mmol cyclohexanol (OL). In addition, 1.90 ml/min of an aqueous phase was added which contained dissolved NaOH (750 mmol NaOH/kg), $Na_2CO_3$ (375 mmol $Na_2CO_3$/kg), $CoSO_4$ (4.3 ppm Co) and a mixture of sodium salts of mono- and di-carboxylic acids ($C_1$ through $C_6$) (15 wt. % in water). Decomposition of the CHHP took place at a temperature of 67° C. in the first reactor and a temperature of 66° C. in the second reactor. Decomposition of the CHHP was monitored by means of an iodometric titration. The first-order velocity constant, calculated over both reactors, was $110*10^{-3}$ min$^{-1}$. CHHP conversion exceeded 93%.

Comparative Example C

Example III was repeated, except that the first reactor was fed at 16.6 ml/min with a cyclohexane oxidation mixture containing, per kilogram, 153 mmol cyclohexyl hydroperoxide (CHHP), 53 mmol cyclohexanone (ON) and 105 mmol cyclohexanol (OL). In addition, 1.94 ml/min of an aqueous phase was added which contained dissolved NaOH (750 mmol NaOH/kg), $Na_2CO_3$ (365 mmol $Na_2CO_3$/kg) and $CoSO_4$ (4.3 ppm Co). Decomposition of the CHHP took place at a temperature of 69° C. in the first reactor and a temperature of 66° C. in the second reactor. Decomposition of the CHHP was monitored by means of an iodometric titration. The first-order velocity constant, calculated over both reactors, was $60*10^{-3}$ min$^{-1}$. CHHP conversion was lower than 87%.

Continuous Reactions At Elevated Pressure

Procedure

The reaction took place in a Cr/Ni steel reactor with a liquid volume of 1000 ml. The reactor was provided with baffles, stirrer, reflux cooler and an overflow. Fresh oxidate and fresh aqueous phase were introduced by two independent pumps. The temperature in the reactor was controlled by a thermostat.

Example VI

The reactor was fed with 75.3 ml/min of a cyclohexane oxidation mixture containing, per kilogram, 153 mmol cyclohexyl hydroperoxide (CHHP), 53 mmol cyclohexanone (ON) and 105 mmol cyclohexanol (OL). In addition, 15.6 ml/min of an aqueous phase was added which contained dissolved NaOH (625 mmol NaOH/kg), $Na_2CO_3$ (445 mmol $Na_2CO_3$/kg), $CoSO_4$ (10 ppm Co) and a mixture of sodium salts of mono- and di-carboxylic acids ($C_1$ through $C_6$) (15 wt. % in water). Decomposition of the CHHP took place at a temperature of 85° C. Decomposition of the CHHP was monitored by means of an iodometric titration. The first-order velocity constant was 1.97 min$^{-1}$ (2.63 min$^{-1}$ at 90° C.). CHHP conversion exceeded 95%.

Example VII

The reactor was fed with 75.3 ml/min of a cyclohexane oxidation mixture containing, per kilogram, 153 mmol cyclohexyl hydroperoxide (CHHP), 53 mmol cyclohexanone (ON) and 105 mmol cyclohexanol (OL). In addition, 15.6 ml/min of an aqueous phase was added which contained dissolved NaOH (935 mmol NaOH/kg), $CoSO_4$ (10 ppm Co) and sodium acetate (12 wt. % in water). Decomposition of the CHHP took place at a temperature of 105° C. Decomposition of the CHHP was monitored by means of an iodometric titration. The first-order velocity constant was 5.65 min$^{-1}$ (2.49 min$^{-1}$ at 90° C.). CHHP conversion exceeded 98%.

Example VIII

The reactor was fed with 76.5 ml/min of a cyclohexane oxidation mixture containing, per kilogram, 153 mmol cyclohexyl hydroperoxide (CHHP), 53 mmol cyclohexanone (ON) and 105 mmol cyclohexanol (OL). In addition, 15.3 ml/min of an aqueous phase was added which contained dissolved NaOH (750 mmol NaOH/kg), $Na_2CO_3$ (315 mmol $Na_2CO_3$/kg), $CoSO_4$ (10 ppm Co) and a mixture of sodium salts of mono- and di-carboxylic acids ($C_1$ through $C_6$) (25 wt. % in water). Decomposition of the CHHP took place at a temperature of 85° C. Decomposition of the CHHP was monitored by means of an iodometric titration. The first-order velocity constant was 1.78 min$^{-1}$ (2.37 min$^{-1}$ at 90° C.). CHHP conversion exceeded 95%.

Comparative Example D

The reactor was fed with 74.5 ml/min of a cyclohexane oxidation mixture containing, per kilogram, 153 mmol cyclohexyl hydroperoxide (CHHP), 53 mmol cyclohexanone (ON) and 105 mmol cyclohexanol (OL). In addition, 15.0 ml/min of an aqueous phase was added which contained dissolved NaOH (660 mmol NaOH/kg), $Na_2CO_3$ (420 mmol $Na_2CO_3$/kg), and $CoSO_4$ (10 ppm Co). Decomposition of the CHHP took place at a temperature of 96° C. Decomposition of the CHHP was monitored by means of an iodometric titration. The first-order velocity constant was 0.45 min$^{-1}$ (0.32 min$^{-1}$ at 90° C.). CHHP conversion was lower than 85%.

Comparative Example E

The reactor was fed with 74.5 ml/min of a cyclohexane oxidation mixture containing, per kilogram, 153 mmol cyclohexyl hydroperoxide (CHHP), 53 mmol cyclohexanone (ON) and 105 mmol cyclohexanol (OL). In addition, 15.0 ml/min of an aqueous phase was added which contained dissolved NaOH (1600 mmol NaOH/kg), $Na_2CO_3$ (630 mmol $Na_2CO_3$/kg) and $CoSO_4$ (10 ppm Co). Decomposition of the CHHP took place at a temperature of 95° C. Decomposition of the CHHP was monitored by means of an iodometric titration. The first-order velocity constant was 0.97 min$^{-1}$ (0.73 min$^{-1}$ at 90° C.). CHHP conversion was lower than 92%.

As can be deduced by comparing the Examples (e.g., the aqueous phase in Example VII contains 12 wt. % sodium acetate) with the Comparative Examples (e.g., the aqueous phase in Comparative Example E contains only 630 mmol/kg $Na_2CO_3$), velocity constants of the cycloalkyl hydroperoxide decomposition reactions are increased in the presence of large amounts of alkali metal salts. For instance, in Example VII and Comparative Example E, the first-order velocity constants at 90° C. are 2.49 min$^{-1}$ and 0.73 min$^{-1}$, respectively. Thus, for the decomposition of cycloalkyl hydroperoxide, addition of alkali metal salts to at least 10 wt. % of the aqueous phase results in an unexpected increase in the reaction velocity.

While the present invention has been described in connection with what is presently considered to be practical and preferred embodiments, it is understood that this invention is not to be limited to the disclosed embodiments of a process for decomposing cycloalkyl hydroperoxides, but on the contrary is intended to cover various modifications and equivalent arrangements included within the spirit and scope of the appended claims.

Thus, it is to be understood that variations in the present invention can be made without departing from the novel aspects of this invention as defined in the claims.

What we claim is:

1. A process for decomposing cycloalkyl hydroperoxide, comprising:
   (a) mixing a first organic phase comprising cycloalkyl hydroperoxide with an aqueous phase comprising one or more alkali metal salts, wherein the alkali metal salts are at least 10% by weight of the aqueous phase, and an alkali metal hydroxide to obtain a reaction mixture; and
   (b) decomposing cycloalkyl hydroperoxide in the reaction mixture by oxidation,
      wherein the alkali metal salts comprise at least one of an alkali metal carbonate, an alkali metal salt of a monocarboxylic acid or an alkali metal salt of a polycarboxylic acid,
      wherein a carboxylic acid moiety of the monocarboxylic acid or the polycarboxylic acid contains 1–24 carbon atoms, and
      wherein the decomposition of cycloalkyl hydroperoxide occurs at a temperature between about 60° C. and about 180° C., and a pressure of about 1 bar to about 6 bar.

2. The process of claim 1, further comprising the steps of:
   (c) separating the aqueous phase from the reaction mixture after decomposition of cycloalkyl hydroperoxide, wherein a separated aqueous phase is obtained; and
   (d) reusing the separated aqueous phase to decompose a second organic phase comprising cycloalkyl hydroperoxide.

3. The process of claim 1, wherein the alkali metal salt is a sodium salt or a potassium salt.

4. The process of claim 1, wherein the reaction mixture has a salt concentration less than 45% by weight of the aqueous phase.

5. The process of claim 4, wherein the salt concentration is between 20–35% by weight of the aqueous phase.

6. The process of claim 1, wherein a sufficient quantity of alkali metal hydroxide is used whereby the aqueous phase has a $[OH^-]$ between 0.1–2 N after decomposition is completed.

7. The process of claim 1, wherein the reaction mixture further comprises between 0.1–1000 parts per million of at least one salt of a transition metal.

8. The process of claim 7, wherein the transition metal is at least one selected from the group consisting of cobalt, chromium, manganese, iron, nickel, copper, and combinations thereof.

9. The process of claim 1, wherein a volume ratio between the aqueous phase and the first organic phase is greater than 0.02.

10. The process of claim 1, wherein the cycloalkyl hydroperoxide is obtained by oxidizing a corresponding cycloalkane at a temperature between 120–200° C. and a pressure between 3–50 bar, wherein no oxidation catalyst is present.

11. The process of claim 1, wherein the cycloalkyl hydroperoxide is obtained by catalyzed oxidation of a corresponding cycloalkane.

12. A process for preparing cycloalkanone and cycloalkanol from a corresponding cycloalkane, comprising the steps of:
   (a) oxidizing the corresponding cycloalkane to cycloalkyl hydroperoxide,
   (b) decomposing the cycloalkyl hydroperoxide as in claim 1, and
   (c) recovering the cycloalkanone and the cycloalkanol from the reaction mixture.

* * * * *